United States Patent
Luithle et al.

(10) Patent No.: US 7,247,728 B2
(45) Date of Patent: Jul. 24, 2007

(54) BICYCLIC N-ARYLAMIDES

(75) Inventors: Joachim Luithle, Wülfrath (DE); Frank-Gerhard Böss, Berkshire (GB); Christina Erb, Kriftel (DE); Timo Flessner, Wuppertal (DE); Martin Hendrix, Odenthal (DE); Marja van Kampen, Neu-Isenburg (DE); Christoph Methfessel, Wuppertal (DE)

(73) Assignee: Bayer Healthcare AG, Leverkusen (DE)

( * ) Notice: Subject to any disclaimer, the term of this patent is extended or adjusted under 35 U.S.C. 154(b) by 40 days.

(21) Appl. No.: 10/497,511

(22) PCT Filed: Dec. 6, 2002

(86) PCT No.: PCT/EP02/13835

§ 371 (c)(1),
(2), (4) Date: Dec. 22, 2004

(87) PCT Pub. No.: WO03/051874

PCT Pub. Date: Jun. 26, 2003

(65) Prior Publication Data

US 2005/0107460 A1 May 19, 2005

(30) Foreign Application Priority Data

Dec. 19, 2001 (DE) ................. 101 62 375

(51) Int. Cl.
*C07D 453/02* (2006.01)
*A61K 31/44* (2006.01)
(52) U.S. Cl. .............. 546/133; 540/582; 514/305; 514/212.01
(58) Field of Classification Search ........... 546/133; 514/305, 212.01; 540/582
See application file for complete search history.

(56) References Cited

U.S. PATENT DOCUMENTS 5,206,235 A * 4/1993 Fisher et al. ............ 514/210.21

FOREIGN PATENT DOCUMENTS

EP 0190920 12/1986
WO 0160821 8/2001

OTHER PUBLICATIONS

Database CA [Online]—Chemical Abstracts Service, Columbus, Ohio, US; Biniecki, Stanislaw, et al., "Synthesis of Quinaldinylamides and Lepidinylamides of Quinuclidine-2-Carboxylic Acid," retrieved from STN Database Accession No. 88:37590. Acta Poloniae Pharmaceutica (1977), 34(2), 125-131.

* cited by examiner

*Primary Examiner*—Shailendra Kumar

(57) ABSTRACT

This application relates to bicyclic N-aryl amides of the formula

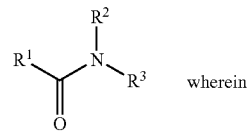 wherein $R^1$ is a 1-aza-bicyclo[3.2.1]octyl group, a 1-aza-bicyclo[2.2.2]oct-3-yl; $R^2$ is an optionally sustituted 8- to 10-membered heteroaryl, naphthyl, or azulenyl group; and $R^3$ is H or $(C_1C_6)$alkyl; or a salt, solvate, or solvate of a salt of these compounds. A process for preparing these compounds, medicaments containing them, and methods for using them in treatment are also disclosed and claimed.

7 Claims, No Drawings

BICYCLIC N-ARYLAMIDES

This application is a 371 of PCT/EP02/13835, filed Dec. 6, 2002.

The invention relates to novel bicyclic N-arylamides, to a process for the preparation thereof and to the use thereof for producing medicaments for the treatment and/or prophylaxis of diseases and for improving perception, concentration, learning and/or memory.

Nicotinic acetylcholine receptors (nAChR) form a large family of ion channels which are activated by the messenger acetylcholine which is produced in the body (Galzi and Changeux, *Neuropharmacol.* 1995, 34, 563–582). A functional nAChR consists of five subunits which may be different (certain combinations of α1–9 and β1–4, γ,δ, ε subunits) or identical (α7–9). This leads to the formation of a diversity of subtypes which differ in the distribution in the muscles, the nervous system and other organs (McGehee and Role, *Annu. Rev. Physiol.* 1995, 57, 521–546). Activation of nAChR leads to influx of cations into the cell and to stimulation of nerve cells or muscle cells. Selective activation of individual nAChR subtypes restricts this stimulation to the cell types which have a corresponding subtype and is thus able to avoid unwanted side effects such as, for example, stimulation of nAChR in the muscles. Clinical experiments with nicotine and experiments in various animal models indicate that central nicotinic acetylchloline receptors are involved in learning and memory processes (e.g. Rezvani and Levin, *Biol. Psychiatry* 2001, 49, 258–267). Nicotinic acetylcholine receptors of the alpha7 subtype (α7 nAChR) have a particularly high concentration in regions of the brain which are important for learning and memory, such as the hippocampus and the cerebral cortex (Séguéla et al., *J. Neurosci.* 1993, 13, 596–604). The α7 nAChR has a particularly high permeability for calcium ions, increases glutamatergic neurotransmission, influences the growth of axons and, in this way, modulates neuronal plasticity (Broide and Leslie, *Mol. Neurobiol.* 1999, 20, 1–16).

Certain quinuclidinecarboxanilides are described as antiarrhythmics and local anesthetics (cf., for example, FR 1.566.045, GB 1 578 421 and Oppenheimer et al. *Life Sci.* 1991, 48, 977–985).

WO 01/60821 discloses biarylcarboxamides with affinity for the α7 nAChR for the treatment of learning and perception impairments.

The present invention relates to compounds of the general formula (I)

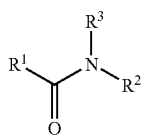

(I)

in which
R$^1$ is a 1-azabicyclo[m.n.p]alkyl radical having 7 to 11 ring atoms, in which m and n are independently of one another 2 or 3,
   in which p is 1, 2 or 3,
   and where the bicycloalkyl radical is optionally substituted by ($C_1$–$C_6$)-alkyl,
R$^2$ is 8- to 10-membered heteroaryl, naphthyl or azulenyl, where the rings are optionally substituted by radicals selected from the group of hydrogen, halogen, formyl, carbamoyl, cyano, trifluoromethyl, trifluoromethoxy, nitro, ($C_1$–$C_6$)-alkyl, ($C_1$–$C_6$)-alkoxy, ($C_1$–$C_6$)-alkylthio, and
R$^3$ is hydrogen or ($C_1$–$C_6$)-alkyl.

The compounds of the invention may exist in stereoisomeric forms which either are related as image and mirror image (enantiomers) or which are not related as image and mirror image (diastereomers). The invention relates both to the enantiomers or diastereomers or respective mixtures thereof. These mixtures are enantiomers and diastereomers which can be separated in a known manner into the stereoisomerically pure constituents.

The compounds of the invention may also be in the form of their salts, solvates or solvates of the salts.

Salts which are preferred for the purposes of the invention are physiologically acceptable salts of the compounds of the invention.

Physiologically acceptable salts of the compounds of the invention may be acid addition salts of the compounds with mineral acids, carboxylic acids or sulphonic acids. Particularly preferred examples are salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, oxalic acid, lactic acid, tartaric acid, citric acid, fumaric acid, maleic acid or benzoic acid.

However, salts which may be mentioned are also salts with conventional bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methylmorpholine, dihydro-abiethylamine, 1-ephenamine or methylpiperidine.

Solvates is the term used for the purposes of the invention for those forms of the compounds which form a complex with solvent molecules by coordination in the solid or liquid state. Hydrates are a special form of solvates in which the coordination takes place with water.

For the purposes of the present invention, the substituents generally have the following meaning:

($C_1$–$C_6$)— and ($C_1$–$C_4$)-alkoxy stands for a straight-chain or branched alkoxy radical respectively having 1 to 6 and 1 to 4 carbon atoms. Preference is given to a straight-chain or branched alkoxy radical having 1 to 4, particularly preferably having 1 to 3, carbon atoms. The following may be mentioned by way of example and preferably: methoxy, ethoxy, n-propoxy, isopropoxy, tert-butoxy, n-pentoxy and n-hexoxy.

($C_1$–$C_6$)— and ($C_1$–$C_4$)-alkyl stand for a straight-chain or branched or branched alkyl radical having 1 to 6 and 1 to 4 carbon atoms. Preference is given to a straight-chain or branched alkyl radical having 1 to 4, particularly preferably having 1 to 3, carbon atoms. The following may be mentioned by way of example and preferably: methyl, ethyl, n-propyl, isopropyl, tert-butyl, n-pentyl and n-hexyl.

($C_1$–$C_6$)-Alkylthio stands for a straight-chain or branched alkylthio radical having 1 to 6 carbon atoms. Preference is given to a straight-chain or branched alkylthio radical having 1 to 4, particularly preferably having 1 to 3, carbon atoms. The following may be mentioned by way of example and preferably: methylthio, ethylthio, n-propylthio, isopropylthio, tert-butylthio, n-pentylthio and n-hexylthio.

The 1-azabicyclo[m.n.p]alkyl radical having 7 to 11 ring atoms is preferably and by way of example: 1-azabicyclo

[3.2.1]octyl (isotropane), 1-azabicyclo[3.3.1]nonyl (isogranatane), 1-azabicyclo[2.2.2]octyl (quinuclidine).

Halogen stands for fluorine, chlorine, bromine and iodine. Fluorine, chlorine and bromine are preferred. Fluorine and chlorine are particularly preferred.

8- to 10-membered heteroaryl stands for an aromatic bicyclic radical having 8 to 10, preferably 9 to 10, ring atoms and up to 5, preferably up to 4, heteroatoms from the series S, O and/or N. The heteroaryl radical may be bonded via a carbon atom or heteroatom. The following may be mentioned by way of example and preferably: indolyl, indazolyl, benzofuranyl, benzothiophenyl, quinolinyl, isoquinolinyl.

If radicals in the compounds of the invention are optionally substituted, the radicals may, unless specified otherwise, be substituted one or more times, identically or differently. Substitution with up to three identical or different substituents is preferred.

Preferred compounds of the general formula (I) are those in which
$R^1$ is 1-azabicyclo[2.2.2]octyl,
and $R^2$ and $R^3$ have the meaning indicated above.

Particularly preferred compounds of the general formula (I) are those in which
$R^1$ is 1-azabicyclo[2.2.2]oct-3-yl,
and $R^2$ and $R^3$ have the meaning indicated above.

Likewise preferred compounds of the general formula (I) are those in which
$R^2$ is 9- to 10-membered heteroaryl or naphthyl, where the rings are optionally substituted by 1 to 3 radicals selected from the group of hydrogen, halogen, cyano, trifluoromethyl, trifluoromethoxy, nitro, $(C_1-C_4)$-alkyl, $(C_1-C_4)$-alkoxy, $(C_1-C_4)$-alkylthio,
and $R^1$ and $R^3$ have the meaning indicated above.

Particularly preferred compounds of the general formula (I) are those in which
$R^2$ is indolyl, benzoimidazolyl, benzotriazolyl, benzothiophenyl, benzofuranyl, quinolinyl, isoquinolyl, benzopyrazinyl, benzopyrimidinyl, benzopyridizanyl or naphthyl, where the rings are optionally substituted by 1 to 3 radicals selected from the group of hydrogen, halogen, cyano, trifluoromethyl, trifluoromethoxy, nitro, $(C_1-C_4)$-alkyl, $(C_1-C_4)$-alkoxy, $(C_1-C_4)$-alkylthio,
and $R^1$ and $R^3$ have the meaning indicated above.

Very particularly preferred compounds of the general formula (I) are those in which
$R^2$ is benzotriazolyl, benzothiophenyl, quinolinyl, benzopyrazinyl or naphthyl, where the rings are optionally substituted by 1 to 3 radicals selected from the group of hydrogen, halogen, cyano, trifluoromethyl, trifluoromethoxy, nitro, $(C_1-C_4)$-alkyl, $(C_1-C_4)$-alkoxy, $(C_1-C_4)$-alkylthio,
and $R^1$ and $R^3$ have the meaning indicated above.

Likewise preferred compounds of the general formula (I) are those in which
$R^3$ is hydrogen or methyl,
and $R^1$ and $R^2$ have the meaning indicated above.

Particularly preferred compounds of the general formula (I) are those in which
$R^3$ is hydrogen,
and $R^1$ and $R^2$ have the meaning indicated above.

Combinations of two or more of the abovementioned preferred ranges are very particularly preferred.

Likewise very particularly preferred are compounds of the general formula (I)

in which
$R^1$ is 1-azabicyclo[2.2.2]oct-3-yl,
$R^2$ is benzotriazolyl, benzothiophenyl, quinolinyl, benzopyrazinyl or naphthyl, where the rings are optionally substituted by 1 to 3 radicals selected from the group of hydrogen, halogen, cyano, trifluoromethyl, trifluoromethoxy, nitro, $(C_1-C_4)$-alkyl, $(C_1-C_4)$-alkoxy, $(C_1-C_4)$-alkylthio,
and
$R^3$ is hydrogen.

The invention further relates to a process for preparing the compounds of the formula (I), characterized in that compounds of the general formula (II)

$$R^1-CO-X \quad (II)$$

in which $R^1$ has the abovementioned meaning, and
X is hydroxyl or a suitable leaving group,
are reacted with a compound of the general formula (III)

$$HNR^1R^2 \quad (III)$$

in which
$R^2$ and $R^3$ have the abovementioned meaning,
in an inert solvent, where appropriate in the presence of a condensing agent and where appropriate in the presence of a base.

If X is a leaving group, chloro, mesyloxy and isobutyloxycarbonyloxy, in particular chloro, are preferred.

Examples of inert solvents are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, or other solvents such as nitromethane, ethyl acetate, acetone, dimethylformamide, dimethylacetamide, 1,2-dimethoxyethane, dimethyl sulfoxide, acetonitrile or pyridine, with preference for tetrahydrofuran, dimethylformamide or chloroform.

Condensing agents are, for example, carbodiimides such as, for example, N,N'-diethyl-, N,N'-dipropyl-, N,N'-diisopropyl-, N,N'-dicyclohexylcarbodiimide, N-(3-di-methylaminoisopropyl)-N'-ethylcarbodiimide hydrochloride (EDC), N-cyclohexyl-carbodiimide-N'-propyloxymethylpolystyrene (PS-carbodiimide) or carbonyl compounds such as carbonyldiimidazole, or 1,2-oxazolium compounds such as 2-ethyl-5-phenyl-1,2-oxazolium-3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxy-tri(dimethyl-amino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU) or benzotriazol-1-yloxytris(dimethylamino)phosphonium hexafluorophosphate (BOP), or mixtures thereof.

It may be advantageous where appropriate to use these condensing agents in the presence of an auxiliary nucleophile such as, for example, 1-hydroxybenzotriazole (HOBt).

Examples of bases are alkali metal carbonates and bicarbonates such as, for example, sodium or potassium carbonate or bicarbonate, or organic bases such as alkylamines, e.g. triethylamine, or N-methylmorpholine, N-methylpiperidine, 4-dimethylamino-pyridine or diisopropylethylamine.

Particular preference is given to the combination of N-(3-dimethylaminoisopropyl)-N'-ethylcarbodiimide hydrochloride (EDC) and/or 1-hydroxybenzotriazole (HOBt) in dimethylformamide.

Particular preference is given to the combination of N,N'-diisopropylcarbodiimide (IDC) and pentafluorophenol in DCM or DMF. The use of tetrafluorophenol and N,N'-diisopropylcarbodiimide (IDC) bonded to resin is likewise particularly preferred (synthetic scheme 1). The preparation of the tetrafluorophenol bonded to resin and the use thereof preferably takes place as described by Salvino et al. *J. Comb. Chem.* 2000, 6, 691–697.

Synthetic scheme 1:

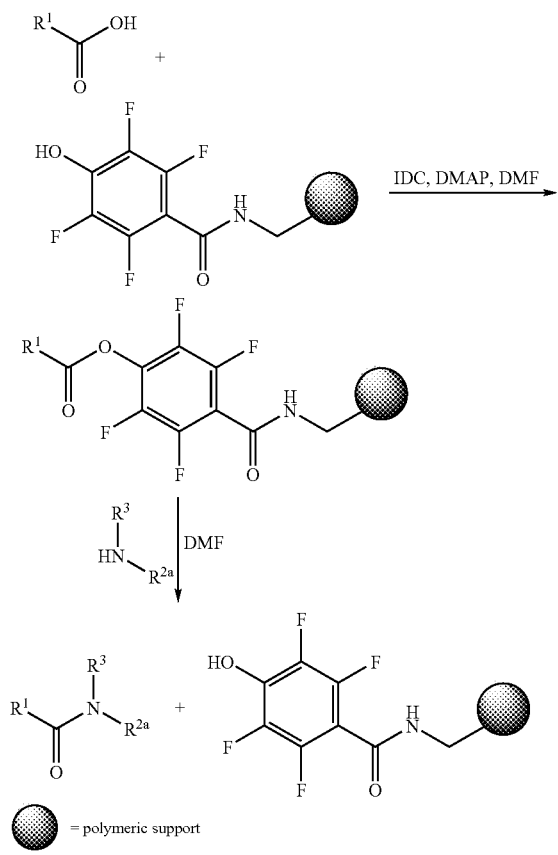

The process of the invention is preferably carried out in a temperature range from room temperature to 50° C. under atmospheric pressure.

The compounds of the general formulae (II) and (III) are known or can be synthesized by known processes from the appropriate precursors (cf., for example, Comprehensive Heterocyclic Chemistry, Katritzki et al., editors.; Elsevier, 1996).

Thus, for example, compounds of the formula (II) can be prepared by processes known from the literature.

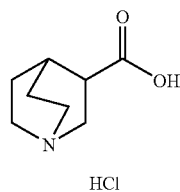

3-Quinuclidinecarboxylic acid hydrochloride: Orlek et al. *J. Med. Chem.* 1991, 34, 2726.

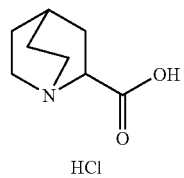

2-Quinuclidinecarboxylic acid hydrochloride: Gassmann and Fox, *J. Org. Chem.* 1967, 32, 480.

Compounds of the formula (III) can be obtained from the corresponding carboxylic acids by reactions known to the skilled worker. Thus, anilines can be prepared by, for example, Curtius or Hoffmann degradation from carboxylic acids or derivatives thereof (cf. for example, Organikum', Wiley-VCH; 1999). It is particularly suitable to use diphenyl phosphorazidate (DPPA) to generate the isocyanate which occurs as intermediate and which subsequently reacts with water to give the target compound. (T. Shioiri and S. Yamada, *Chem. Pharm. Bull.* 1974, 22, 859; Shioiri et al. *J. Am. Chem. Soc* 1972, 94, 6203.

Synthetic scheme 2:

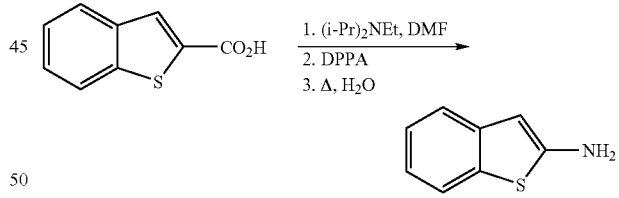

The compounds of the invention of the general formula (I) are suitable for use as medicaments for the treatment and/or prophylaxis of diseases in humans and/or animals.

The compounds of the invention show a valuable range of pharmacological effects which could not have been predicted.

They are notable as ligands, especially agonists, on the α7 nAChR.

The compounds of the invention can, because of their pharmacological properties, be employed alone or in combination with other medicaments for the treatment and/or prevention of cognitive impairments, especially of Alzheimer's disease. Because of their selective effect as α7 nAChR agonists, the compounds of the invention are particularly suitable for improving perception, concentration, learning or memory, especially after cognitive impairments like those occurring for example in situations/diseases/syndromes such as mild cognitive impairment, age-associated learning and memory impairments, age-associated memory loss, vascular dementia, craniocerebral trauma, stroke, dementia occurring after strokes (post-stroke dementia), post-traumatic craniocerebral trauma, general concentration impairments, concentration impairments in children with learning and memory problems, attention deficit hyperactivity disorder, Alzheimer's disease, vascular dementia, Lewy body dementia, dementia with degeneration of the frontal lobes, including Pick's syndrome, Parkinson's disease, progressive nuclear palsy, dementia with corticobasal degeneration, amyotrophic lateral sclerosis (ALS), Huntington's disease, multiple sclerosis, thalamic degeneration, Creutzfeld-Jacob dementia, HIV dementia, schizophrenia, schizophrenia with dementia or Korsakoffs psychosis.

The compounds of the invention can be employed alone or in combination with other medicaments for the prophylaxis and treatment of acute and/or chronic pain (for a classification, see "Classification of Chronic Pain, Descriptions of Chronic Pain Syndromes and Definitions of Pain Terms", 2nd edition, Meskey and Begduk, editors; IASP Press, Seattle, 1994), especially for the treatment of cancer-induced pain and chronic neuropathic pain like, for example, that associated with diabetic neuropathy, postherpetic neuralgia, peripheral nerve damage, central pain (for example as a consequence of cerebral ischaemia) and trigeminal neuralgia, and other chronic pain such as, for example, lumbago, backache (low back pain) or rheumatic pain. In addition, these active ingredients are also suitable for the therapy of primary acute pain of any origin and of secondary states of pain resulting therefrom, and for the therapy of states of pain which were formerly acute and have become chronic.

The in vitro effect of the compounds of the invention can be shown in the following assays:

1. Determination of the Affinity of Test Substances for α7 nAChR by Inhibition of [$^3$H]-methyllycaconitine Binding to Rat Brain Membranes The [$^3$H]-methyllycaconitine binding assay is a modification of the method described by Davies et al. (*Neuropharmacol.* 1999, 38, 679–690).

Rat brain tissue (hippocampus or whole brain) is homogenized in homogenization buffer (10% w/v, 0.32 M sucrose, 1 mM EDTA, 0.1 mM phenylmethylsulphonyl fluoride (PMSF), 0.01% (w/v) NaN$_3$, pH 7.4, 4° C.) at 600 rpm in a glass homogenizer. The homogenate is centrifuged (1000×g, 4° C., 10 min) and the supernatant is removed. The pellet is resuspended (20% w/v) and the suspension is centrifuged (1000×g, 4° C., 10 min). The two supernatants are combined and centrifuged (15 000×g, 4° C., 30 min). The pellet obtained in this way is referred to as the P2 fraction.

The P2 pellet is washed twice with binding buffer (50 mM Tris-HCl, 1 mM MgCl$_2$, 120 mM NaCl, 5 mM KCl, 2 mM CaCl$_2$, pH 7.4), and centrifuged (15 000×g, 4° C., 30 min).

The P2 membranes are resuspended in binding buffer and incubated in a volume of 250 µl (amount of membrane protein 0.1–0.5 mg) in the presence of 1–5 nM [$^3$H]-methyllycaconitine 0.1% (w/v) BSA (bovine serum albumin) and various concentrations of the test substance at 21° C. for 2.5 h. The non-specific binding is determined by incubation in the presence of 1 µM α-bungarotoxin or 100 µM nicotine or 10 µM MLA (methyllycaconitine).

The incubation is stopped by adding 4 ml PBS (20 mM Na$_2$HPO$_4$, 5 mM KH$_2$PO$_4$, 150 mM NaCl, pH 7.4, 4° C.) and filtering through type A/E glass fibre filters (Gelman Sciences) which have previously been placed in 0.3% (v/v) polyethyleneimine (PEI) for 3 h. The filters are washed twice with 4 ml of PBS (4° C.), and the bound radioactivity is determined by scintillation measurement. All the assays are carried out in triplicate. The dissociation constant K$_i$ of the test substance was determined from the IC$_{50}$ of the compounds (concentration of the test substance at which 50% of the ligand bound to the receptor is displaced), the dissociation constant K$_D$ and the concentration L of [$^3$H]-methyllycaconitine using the equation K$_i$=IC$_{50}$/(1+L/K$_D$).

In place of [$^3$H]-methyllycaconitine it is also possible to employ other α7 nAChR-selective radioligands such as, for example, [$^{125}$I]-α-bungarotoxin or nonselective nAChR radioligands together with inhibitors of other nAChRs.

The suitabilitiy of the compounds of the invention for the treatment of cognitive impairments can be shown in the following animal models:

2. Object Recognition Test

The object recognition test is a memory test. It measures the ability of rats (and mice) to distinguish between familiar and unfamiliar objects.

The test is carried out as described by Blokland et al., *NeuroReport* 1998, 9, 4205–4208; A. Ennaceur, J. Delacour,. *Behav. Brain Res.* 1988, 31, 47–59; A. Ennaceur, K. Meliani., *Psychopharmacology* 1992, 109, 321–330; and Prickaerts et al., *Eur. J. Pharmacol.* 1997, 337, 125–136.

In a first run, a rat is confronted in an otherwise empty observation arena of relatively large size by two identical objects. The rat will investigate, i.e. sniff round and touch, both objects extensively. In a second run, after an interval of 24 hours, the rat is put in the observation arena again. One of the familiar objects has now been replaced by a new, unfamiliar object. If a rat recognizes the familiar object, it will concentrate on investigating the unfamiliar object. However, after 24 hours, a rat has normally forgotten which object it investigated in the first run, and it will therefore inspect both objects to the same extent. Administration of a substance with a learning-and memory-improving effect may lead to a rat recognizing the object seen in the first run 24 hours previously as familiar. It will investigate the new, unfamiliar object in more detail than the familiar one. This memory ability is expressed in a discrimination index. A discrimination index of zero means that the rat investigates both objects, the old and the new, for equal times; that is to say it has not recognized the old object and reacts to both objects as if they were unfamiliar and new. A discrimination index greater than zero means that the rat inspects the new object longer than the old one; that is to say the rat has recognized the old object.

3. Social Recognition Test:

The social recognition test is a test to examine the learning- or memory-improving effect of test substances.

Adult rats housed in groups are placed singly in test cages 30 minutes before the start of the test. Four minutes before the start of the test, the test animal is put in an observation box. After this adaptation time, a juvenile animal is put in with the test animal and the time for which the adult animal investigates the juvenile animal is measured for 2 minutes (trial 1). All behaviours clearly directed at the young animal are measured, i.e. anogenital inspection, pursuit and fur care, during which the old animal is no further than 1 cm from the young animal. The juvenile animal is then taken out, and the adult is left in its test cage (for 24-hour retention, the animal is returned to its home cage). The test animal is treated with substance before or after the first test. Depending on the timing of the treatment, the learning or the storage of the information about the young animal can be influenced by the substance. After a fixed period (retention), the test is repeated (trial 2). A larger difference between the investigation times measured in trials 1 and 2 means that the adult animal has remembered the young animal better.

The compounds of the invention of the general formula (I) are suitable for use as medicaments for humans and animals.

The present invention also includes pharmaceutical preparations which, besides inert, nontoxic, pharmaceutically suitable excipients and carriers, contain one or more compounds of the general formula (I), or which consist of one or more compounds of the formula (I), and to processes for producing these preparations.

The compounds of the formula (I) are to be present in these preparations in a concentration of from 0.1 to 99.5% by weight, preferably from 0.5 to 95% by weight, of the complete mixture.

Besides the compounds of the formula (I), the pharmaceutical preparations may also contain other active pharmaceutical ingredients.

The abovementioned pharmaceutical preparations can be produced by known methods in a conventional way, for example using the excipient(s) or carrier(s).

The novel active ingredients can be converted in a known manner into conventional formulations such as tablets, coated tablets, pills, granules, aerosols, syrups, emulsions, suspensions and solutions, using inert, nontoxic, pharmaceutically suitable carriers or solvents. In these cases, the therapeutically active compound should in each case be present in a concentration of about 0.5 to 90% by weight of the complete mixture, i.e. in amounts which are sufficient to reach the stated dose range.

The formulations are produced for example by extending the active ingredients with solvents and/or carriers, where appropriate with use of emulsifiers and/or dispersants, it being possible for example when water is used as diluent where appropriate to use organic solvents as auxiliary solvents.

Administration can take place in a conventional way, preferably orally, transdermally or parenterally, especially perlingually or intravenously. However, it can also take place by inhalation through the mouth or nose, for example with the aid of a spray, or topically via the skin.

It has generally proved advantageous to administer amounts of about 0.001 to 10 mg/kg, on oral administration preferably about 0.005 to 3 mg/kg, of body weight to achieve effective results.

It may, nevertheless, be necessary where appropriate to deviate from the stated amounts, in particular as a function of the body weight or of the mode of administration, of the individual behavior towards the medicament, the nature of its formulation and the time or interval over which administration takes place. Thus, it may be sufficient in some cases to make do with less than the aforementioned minimum amount, whereas in other cases the stated upper limit must be exceeded. Where larger amounts are administered, it may be advisable to divide these into a plurality of single doses over the day.

Abbreviations:

| | |
|---|---|
| DMF | N,N-Dimethylformamide |
| DMSO | Dimethyl sulfoxide |
| HOBt | 1-Hydroxy-1H-benzotriazole × $H_2O$ |
| NMR | Nuclear magnetic resonance spectroscopy |
| RT | Room temperature |
| TBTU | O-(Benzotriazol-1-yl)-N,N,N',N'-tetramethyluronium tetrafluoroborate |
| THF | Tetrahydrofuran |

LC-MS Method:

| MS apparatus type: | Micromass Platform LCZ Ionization: ESI positive |
|---|---|
| HPLC apparatus type: | HP 1100 UV detector DAD: 208–400 nm Oven temp.: 40° C. |
| Column: | Symmetry C 18 50 mm × 2.1 mm; 3.5 μm |

| Gradient: | | | |
|---|---|---|---|
| Time (min) | A: % | B: % | Flow rate (ml/min) |
| 0.00 | 10.0 | 90.0 | 0.50 |
| 4.00 | 90.0 | 10.0 | 0.50 |
| 6.00 | 90.0 | 10.0 | 0.50 |
| 6.10 | 10.0 | 90.0 | 1.00 |
| 7.50 | 10.0 | 90.0 | 0.50 |

A: Acetonitrile + 0.1% formic acid
B: Water + 0.1% formic acid

Starting Compounds:

EXAMPLE 1 A

3-Quinuclidinecarbonyl Chloride Hydrochloride

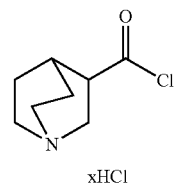

3-Quinuclidinecarboxylic acid hydrochloride was prepared as described by Orlek et al. *J. Med. Chem.* 1991, 34, 2726.

500 mg (2.61 mmol) of 3-quinuclidinecarboxylic acid are heated together with 1.9 ml (26.09 mmol) of thionyl chloride under reflux for 2 h. The reaction mixture is freed of excess thionyl chloride under reduced pressure. 20 ml portions of toluene are added twice and evaporated to dryness each time. The product obtained in this way is reacted immediately without further purification.

EXAMPLE 2 A

7-Bromo-1-benzothiophen-2-amine

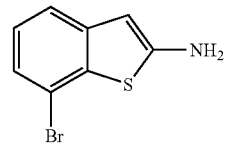

156 mg (0.61 mmol) of 7-bromo-1-benzothiophene-2-carboxylic acid are mixed with 156.8 mg (1.21 mmol) of N,N-diisopropylethylamine in 4.0 ml of DMF. At 0° C., 183.7 mg (0.67 mmol) of diphenyl phosphorazidate are added. The reaction mixture is left to stand at 8° C. overnight and then stirred into ice-water. It is neutralized with acetic acid, and the resulting precipitate is filtered off with suction and carefully dried at 40° C. The solid is then suspended in xylene and heated under reflux for 1 h. The solvent is removed under reduced pressure, and the residue is put in water and heated for 3 h. The aqueous phase is extracted several times with ethyl acetate. The organic phase is dried over sodium sulfate and then the solvent is removed under reduced pressure. 128 mg of the title compound are isolated in a purity which is suitable for further reactions. The amine is reacted further without further purification.

LC-MS: $R_t$=5.25 min., MS (ESIpos): m/z=229 (M+H)$^+$.

Exemplary Embodiments

EXAMPLE 1

N-(2-Naphthyl)quinuclidine-3-carboxamide Hydrochloride

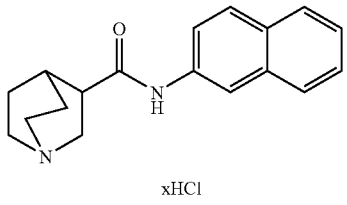

xHCl 740 mg (5.14 mmol) of 2-naphthylamine are added to a solution of 540 mg (2.57 mmol) of 3-quinuclidinecarbonyl chloride hydrochloride and pyridine (620 mg, 4.8 mmol) in 3 ml of dimethylformamide at 0° C. The mixture is stirred at RT over night. It is worked up by concentrating and taken up in dichloromethane. The crude product is chromatographed on silica gel (mobile phase: dichloromethane/methanol 10:1, 5:1). The resulting product crystallizes from dichloromethane and is filtered off with suction and dried.

Yield: 26% of theory of the hydrochloride $^1$H-NMR (200,1 MHz, DMSO-d$_6$): δ=10.60 (br. s, 1H), 10.10 (br. s, 1H), 8.35 (d, 1H), 7.95–7.75 (m, 3H), 7.65 (dd, 1H), 7.60–7.45 (m, 2H), 3.65 (m, 1H), 3.45–,10 (m, 7H), 2.05–1.85 (m, 2H), 1.85–1.70 (m, 2H)

MS (ESIpos): m/z=281 (M+H)$^+$ (free base)

LC-MS: $R_t$=2.65 min., MS (ESIpos): m/z=281 (M+H)$^+$ (free base).

EXAMPLE 2

N-(6-Quinolinyl)quinuclidine-3-carboxamide Hydrochloride

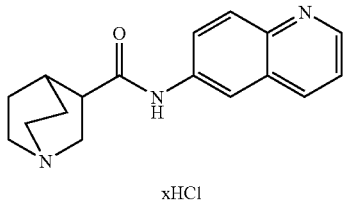

xHCl 172 mg (1.19 mmol) of 6-aminoquinoline are mixed with 461 mg (3.57 mmol) of N,N-diisopropylethylamine in 3 ml of DMF under argon at 0° C. 250 mg (2.57 mmol) of 3-quinuclidinecarbonyl chloride hydrochloride are dissolved in a little dry DMF and added dropwise to the reaction mixture at 0° C. It is then stirred at room temperature overnight. It is worked up by concentrating and taking up in dichloromethane. The crude product is chromatographed on silica gel 60 (mobile phase: dichloromethane/ethyl acetate 10:1, then dichloromethane/methanol 10:1, 3:1). The product fractions are combined and finally purified by preparative HPLC (RP18 column; mobile phase: acetonitrile/water, gradient 1:99→30:70).

Yield: 28 mg (7% of theory) of the hydrochloride $^1$H-NMR (200,1 MHz, DMSO-d$_6$): δ=11.00 (br. s, 1H), 10.19 (br. s, 1H), 9.06–9.04 (m, 1H), 8.88–8.85 (m, 1H), 8.70–8.68 (m, 1H), 8.27–8.23 (m, 1H), 8.12–8.06 (m, 1H), 7.89–7.83 (m, 1H), 3.70–3.50 (m, 1H), 3.40–3.10 (m, 7H), 2.00–1.80 (m, 2H), 1.80–1.65 (m, 2H)

MS (ESIpos): m/z=282 (M+H)$^+$ (free base)

LC-MS: $R_t$=0.30 min., MS (ESIpos): m/z=282 (M+H)$^+$ (free base).

EXAMPLE 3

N-(3a,7a-Dihydro-1H-indazol-6-yl)quinuclidine-3-carboxamid Hydrochloride

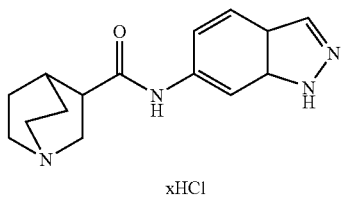

xHCl

In analogy to the method described in Example 2, 250 mg (2.57 mmol) of 3-quinuclidinecarbonyl chloride, 461 mg (3.57 mmol) of N,N-diisopropylethylamine, catalytic amounts of DMAP (approx. 1 mg) and 158 mg (1.19 mmol) of 4-aminoindazole are reacted.

Yield: 55 mg (15% of theory) of the hydrochloride $^1$H-NMR (200,1 MHz, DMSO-d$_6$): δ=10.55 (br. s, 1H), 10.05 (br. s, 1H), 8.15 (s, 1H), 7.97 (d, 1H), 7.67 (d, 1H), 7.14 (dd, 1H), 3.70–3.60 (m, 1H), 3.40–3.15 (m, 7H), 2.00–1.85 (m, 2H), 1.80–1.65 (m, 2H)

MS (ESIpos): m/z=271 (M+H)$^+$ (free base).

EXAMPLE 4

N-(6-Quinoxalinyl)quinuclidine-3-carboxamide Hydrochloride

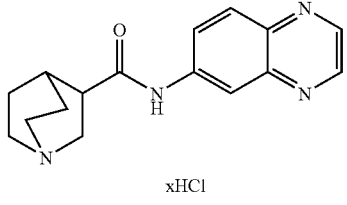

xHCl

In analogy to the method described in Example 2, 250 mg (2.57 mmol) of 3-quinuclidinecarbonyl chloride, 461 mg (3.57 mmol) of N,N-diisopropylethylamine, catalytic amounts of DMAP (approx. 1 mg) and 173 mg (1.19 mmol) of 6-quinoxalinylamine are reacted.

Yield: 58 mg (15% of theory) of the Hydrochloride $^1$H-NMR (200,1 MHz, DMSO-d$_6$): δ=10.90 (s, 1H), 9.99 (br. s, 1H), 8.90–8.88 (m, 2H), 8.84–8.83 (m, 2H), 8.10–7.94 (m, 2H), 3.60–3.50 (m, 1H), 3.30–3.05 (m, 7H), 2.00–1.80 (m, 2H), 1.80–1.65 (m, 2H)

MS (ESIpos): m/z=283 (M+H)$^+$ (free base).

What is claimed is:

1. A compound of the general formula (I)

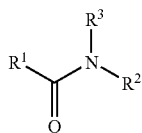

in which
- $R^1$ is a 1-aza-bicyclo[3.2.1]octyl, 1-aza-bicyclo[3.3.1]nonyl, or 1-aza-bicyclo[2.2.2]oct-3-yl, wherein the bicycloalkyl radical is optionally substituted by $(C_1-C_6)$-alkyl,
- $R^2$ is 8- to 10-membered heteroaryl, naphthyl or azulenyl, where the rings are optionally substituted by radicals selected from the group of hydrogen, halogen, formyl, carbamoyl, cyano, trifluoromethyl, trifluoromethoxy, nitro, $(C_1-C_6)$-alkyl, $(C_1-C_6)$-alkoxy, $(C_1-C_6)$-alkylthio, and
- $R^3$ hydrogen or $(C_1-C_6)$-alkyl, or their salts, solvates and solvates of the salts.

2. The compound of claim 1, where
$R^1$ is 1-azabicyclo[2.2.2]oct-3-yl,
and $R^2$ and $R^3$ have the meaning indicated in claim 1.

3. The compound of claim 1 or 2, where
$R^1$ is 1-azabicyclo[2.2.2]oct-3-yl,
$R^2$ is benzotriazolyl, benzothiophenyl, quinolinyl, benzopyrazinyl or naphthyl, where the rings are optionally substituted by 1 to 3 radicals selected from the group of hydrogen, halogen, cyano, trifluoromethyl, trifluoromethoxy, nitro, $(C_1-C_4)$-alkyl, $(C_1-C_4)$-alkoxy, $(C_1-C_4$-alkylthio, and
$R^3$ is hydrogen.

4. A process for preparing compounds of the general formula (I) as claimed in claim 1, characterized in that compounds of the general formula (II)

in which
$R^1$ has the meaning indicated in claim 1, and
X is hydroxyl or a suitable leaving group,
are reacted with a compound of the general formula (III)

in which
$R^2$ and $R^3$ have the meaning indicated in claim 1,
in an inert solvent, where appropriate in the presence of a condensing agent and where appropriate
in the presence of a base.

5. Medicament comprising at least one compound according to claim 1 mixed with at least one pharmaceutically acceptable, essentially nontoxic carrier or excipient.

6. A method for the treatment and/or prophylaxis of impairments of perception, concentration, learning and/or memory comprising administering to a subject an effective amount of a compound of claim 1.

7. A method for the treatment and/or prophylaxis of impairments of perception, concentration, learning and/or memory comprising administering to a subject an effective amount of a compound of claim 5.

* * * * *